(12) United States Patent
McCormick

(10) Patent No.: US 11,701,306 B2
(45) Date of Patent: Jul. 18, 2023

(54) NATURAL TOOTH POWDER TABLETS

(71) Applicant: Lindsay McCormick, Los Angeles, CA (US)

(72) Inventor: Lindsay McCormick, Los Angeles, CA (US)

(*) Notice: Subject to any disclaimer, the term of this patent is extended or adjusted under 35 U.S.C. 154(b) by 0 days.

(21) Appl. No.: 16/459,828

(22) Filed: Jul. 2, 2019

(65) Prior Publication Data

US 2020/0009022 A1 Jan. 9, 2020

Related U.S. Application Data

(60) Provisional application No. 62/694,694, filed on Jul. 6, 2019.

(51) Int. Cl.
| | |
|---|---|
| *A61K 8/02* | (2006.01) |
| *A61Q 11/00* | (2006.01) |
| *A61K 8/46* | (2006.01) |
| *A61K 8/25* | (2006.01) |
| *A61K 8/19* | (2006.01) |
| *A61K 8/34* | (2006.01) |
| *A61K 8/92* | (2006.01) |
| *A61K 8/24* | (2006.01) |

(52) U.S. Cl.
CPC .............. *A61K 8/0225* (2013.01); *A61K 8/19* (2013.01); *A61K 8/24* (2013.01); *A61K 8/25* (2013.01); *A61K 8/345* (2013.01); *A61K 8/466* (2013.01); *A61K 8/922* (2013.01); *A61Q 11/00* (2013.01); *A61K 2800/28* (2013.01)

(58) Field of Classification Search
CPC ........ A61K 8/0225; A61K 8/466; A61K 8/25; A61K 8/19; A61K 8/345; A61K 8/922; A61K 8/24; A61K 2800/28; A61K 2800/41; A61Q 11/00
See application file for complete search history.

(56) References Cited

U.S. PATENT DOCUMENTS

| | | |
|---|---|---|
| 3,342,687 A | 9/1967 | Gould |
| 3,932,604 A | 1/1976 | Barth |
| 4,308,252 A | 12/1981 | Tomaich et al. |
| 4,765,984 A | 8/1988 | Vellekoop et al. |
| 5,089,255 A | 2/1992 | Gaffar et al. |
| 5,496,541 A | 3/1996 | Cutler |
| 5,804,165 A | 9/1998 | Arnold |
| 6,054,119 A | 4/2000 | Hurme et al. |
| 6,207,138 B1 | 3/2001 | Zhang et al. |
| 6,238,648 B1 | 5/2001 | Leusch et al. |
| 8,603,440 B2 | 12/2013 | Andersen et al. |
| 8,623,331 B2 | 1/2014 | Andersen et al. |
| 8,722,022 B2 | 5/2014 | Andersen et al. |
| 8,858,920 B2 | 10/2014 | Robinson et al. |
| 8,961,938 B2 * | 2/2015 | Kato ...................... A61Q 11/00 424/49 |
| 8,968,770 B2 | 3/2015 | Pedersen et al. |
| 9,283,191 B2 | 3/2016 | Andersen et al. |
| 2004/0101493 A1 * | 5/2004 | Scott ..................... A61K 8/8117 424/49 |
| 2005/0244343 A1 | 11/2005 | Withiam et al. |
| 2005/0244492 A1 | 11/2005 | Mehra et al. |
| 2006/0045851 A1 | 3/2006 | Fitzgerald et al. |
| 2006/0275223 A1 * | 12/2006 | Burr ....................... A61Q 11/00 424/49 |
| 2007/0196477 A1 | 8/2007 | Withiam et al. |
| 2007/0254067 A1 | 11/2007 | Ha |
| 2008/0253976 A1 | 10/2008 | Scott et al. |
| 2009/0087501 A1 | 4/2009 | Cummins |
| 2010/0255064 A1 | 10/2010 | Andersen et al. |
| 2014/0227202 A1 | 8/2014 | Pilgaonkar et al. |
| 2014/0345648 A1 * | 11/2014 | Abdalla ................. A61K 33/20 134/7 |
| 2018/0140521 A1 * | 5/2018 | Geonnotti ............ A61K 9/2018 |

FOREIGN PATENT DOCUMENTS

| | | |
|---|---|---|
| WO | 98/10110 A1 | 3/1998 |
| WO | 2012/012385 A2 | 1/2012 |

OTHER PUBLICATIONS

Written Opinion and International Search Report dated Oct. 23, 2019 issued in corresponding International Patent Application No. PCT/US2019/040245.
International Preliminary Report on Patentability dated Jan. 12, 2021, issued in corresponding International Patent Application No. PCT/US2019/040245 (8 pgs.).

* cited by examiner

*Primary Examiner* — Snigdha Maewall
(74) *Attorney, Agent, or Firm* — Pillsbury Winthrop Shaw Pittman, LLP

(57) ABSTRACT

Disclosed are compositions that include a combination of natural tooth powder ingredients pressed into tablet form, and methods of making the composition, and to methods of enhancing dental hygiene that includes administration of the composition. The compositions include natural ingredients such as xylitol and at least one tooth cleaning agent, and can be formed into a tablet suitable for cleaning the teeth without the use of a toothbrush or water.

7 Claims, No Drawings

NATURAL TOOTH POWDER TABLETS

CROSS REFERENCE TO RELATED APPLICATIONS

This application claims the benefit of priority to U.S. Provisional Patent Application No. 62/694,694, filed Jul. 6, 2019, which is expressly incorporated by reference in its entirety.

FIELD

The embodiments relate to a composition that includes a combination of natural tooth powder ingredients pressed into tablet form, to methods of making the composition, and to methods of enhancing dental hygiene that includes administration of the composition.

BACKGROUND

Maintaining oral hygiene is necessary in preventing gum and mouth diseases and keeping teeth healthy and attractive. The dental care industry is dedicated to facilitating oral hygiene, including cleaning and whitening teeth, freshening breath, and intensive preventive care for various oral diseases. There are numerous oral care compositions in a variety of forms that can be used by consumers to assist in maintaining oral hygiene.

Most of these compositions are in gel or paste form made with glycerine, hydrated silica and sorbitol and include synthetic chemicals like sodium lauryl sulfate (SLS). Other compositions are available in powder form with a sodium bicarbonate base to provide effervescence when chewed.

Crest® and Colgate® brands have many products for use in cleaning the mouth, gums and teeth, and that protect tooth enamel in paste and powder form. Some of the components used in these products, however, have been known to cause ulcers on the tongue and gums and other problems when used over long periods of time. The products also often contain artificial dyes and preservatives. Many people currently avoid artificial and synthetic products and wish to purchase products that are made with more natural ingredients, while at the same time with to purchase products that have a pleasant taste.

Some natural tooth powder companies, including Lush Cosmetics® and Eco Dent®, offer SLS-free formulations that include tooth powder or pressed tablets, but some of these formulations include sorbitol, an ingredient avoided by consumers due to bloating, gas and irritation, as well as color and filler ingredients like titanium dioxide which consumers may avoid due to health risks. Powder dentifrice forms also are messy and unhygienic when used by dipping a wet toothbrush into the powder for application. Both Lush Cosmetics® and Eco Dent® products also include sodium bicarbonate, which some consumers avoid due to its abrasiveness to enamel when present in high concentrations. In addition, it is difficult to unmask the flavor of such products, even with the use of essential oils or synthetic sweeteners, and neither product offers a fluoride option that many customers desire.

In addition to the products currently on the market, a number of documents exist that disclose various dentifrice products. For example, U.S. Pat. No. 3,342,687 discloses oral preparations containing an anti-microbial agent. A chewable tablet is disclosed, having the following formulation:

| CHEWABLE TABLET FOR BRUSHING | Parts |
| --- | --- |
| Insoluble sodium metaphosphate | 32.59 |
| Dicalcium phosphate dihydrate | 4.03 |
| Poly(ethylene glycol) MW about 6000 | 5.00 |
| Saccharine | 0.25 |
| Sodium carboxymethylcellulose | 1.25 |
| Sodium lauryl Sulfate | 2.25 |
| Starch | 3.0 |
| Mannitol | 47.3 |
| Talc | 0.5 |
| Magnesium stearate | 1.25 |
| Flavor, color, etc. | 2.48 |
| Antimicrobial agent of Example 1 | 0.1 |

The tablet is employed as a dentifrice by introducing into the mouth a tablet thereof having a weight of about 0.5 grams, crushing it between the teeth, and then brushing the teeth in the usual fashion with saliva acting as a fluid vehicle for the crushed tablet particles.

U.S. Pat. No. 5,089,255 discloses a dentifrice that includes xylitol and fluoride ions. The disclosed dentifrice is said to be useful in remineralizing demineralized portions of teeth by treatment with a non-astringent composition containing about 10-20% xylitol, and at least one fluoride ion-providing compound in a total amount sufficient to provide about 150 ppm to about 1800 ppm of fluoride ions, with sodium fluoride providing a predominant proportion of such fluoride ions. U.S. Pat. No. 3,932,604 also discloses dentifrices that include xylitol. The dentifrice contains non-cariogenic xylitol which has the sweetening strength of sucrose and which also serves as a humectant.

U.S. Pat. No. 5,496,541 (the "'541 patent") discloses the use of xylitol in dentifrice compositions. Xylitol-containing toothpastes have been sold for many years. The most common Xylitol concentration in current European toothpastes is 10 percent by weight. The most common surfactant is Sodium lauryl Sulfate (SLS). The '541 patent states that there are presently no commercial toothpaste products containing at least 10 percent by weight of Xylitol, plus a mild Surfactant and no SLS.

U.S. Patent Application Publication No. 2009/0087501 discloses oral compositions having at least two botanical active ingredients derived from plants. The oral composition also includes an orally acceptable vehicle to deliver an effective amount of the at least two active ingredients in vivo. The botanical active ingredients provide particularly efficacious antimicrobial (antibacterial, antiviral, and/or antifungal), antioxidant, anti-inflammatory, anti-ageing, and/or healing properties to the oral compositions. The '501 publication discloses that the oral composition is in the form of a lozenge, bead, tablet or chewing gum or other similar solid delivery system. Such delivery systems are well known and generally entail stirring the active antioxidant agent into a warm base with flavor, and non-cariogenic sweeteners. The '501 publication further discloses the orally acceptable vehicle or carrier in a lozenge bead or tablet is a non-cariogenic, solid water-soluble poly-hydric alcohol (polyol) such as mannitol, xylitol, sorbitol, malitol, hydrogenated starch hydrozylate, hydrogenated glucose, hydrogenated disaccharides or hydrogenated polysaccharides, in an amount of about 85 to about 95% of the total composition. Emulsifiers such as glycerin, and tableting lubricants, in minor amounts of about 0.1 to 5%, may be incorporated into the tablet, bead or lozenge formulation to facilitate the preparation of the tablet beads and lozenges. Suitable lubricants include vegetable oils such as coconut oil, magnesium Stearate, aluminum Stearate, talc, starch and Carbowax.

Suitable non-cariogenic gums include kappa carrageenan, carboxymethyl cellulose, hydroxyethyl cellulose and the like.

U.S. Patent Application Publication No. 2008/00253976 discloses personal care compositions, including compositions for oral, throat and skin care comprising a blend of naturally occurring flavor or perfume ingredients or essential oils containing such ingredients, wherein the blend provides excellent antimicrobial activity and comprises at least two components, a first acyclic component selected from citral neral, geranial, geraniol and nerol and a second cyclic-containing component selected from eucalyptol, carvacrol and eugenol. The blend disclosed in the '976 publication includes 3, 4, 5 or more of the above components. The '976 publication discloses compositions that are effective in killing, suppressing the growth of, and/or altering metabolism of microorganisms including those that cause undesirable oral cavity conditions including plaque, caries, calculus, gingivitis, periodontal disease and malodor. Optionally the blend further comprises additional antimicrobial and/or anti-inflammatory components, preferably naturally-occurring as well.

U.S. Patent Application Publication No. 2006/0045851 discloses an essential oil composition comprising at least two essential oils selected from Group A, which includes mint and spice essential oils and at least one essential oil selected from Group B, which includes citrus essential oils. The '851 publication discloses that the essential oil composition can effectively kill and remove oral microbials which are correlated to the formation of biofilm in the oral cavity, and that the essential oil composition can be combined with a variety of oral carriers and actives.

WO 2012/012385 discloses compositions containing one or more derivatives of essential oil compounds for use in personal care compositions, such as compositions for oral, throat and skin care. These derivatives include acetals of parent essential oil aldehydes and ketones; esters or ethers of parent essential oil alcohols and phenolics; and esters of parent essential oil acids. Examples of parent essential oil aldehydes and ketones include citral, cinnamic aldehyde, p-anisaldehyde, vanillin, ethyl vanillin, heliotropin, carvone, and menthone. Examples of parent essential oil alcohols and phenolics include thymol, eugenol, isoeugenol, dihydroeugenol, carvacrol, carveol, geraniol, nerol, vanillyl alcohol, heliotropyl alcohol, p-anisyl alcohol, cinnamyl alcohol and β-ionol. Examples of parent essential oil acids include ρ-anisic acid, cinnamic acid, vanillic acid and geranic acid. The compositions comprising essential oil derivatives are useful as base flavor or base perfume for incorporation into personal care products and to provide other benefits including antimicrobial efficacy. The compositions also can contain additional antimicrobially or anti-inflammatory-effective components including those also derived from plant essential oils or synthetic versions thereof.

WO 1998/010110 discloses substantially water free tablets that, when chewed in the mouth form a self-foaming paste containing stannous fluoride. The tablet contains less than about 50% by weight of a composition producing carbon dioxide when mixed with the saliva in the mouth, and greater than about 35% by weight of a substantially insoluble filling and polishing composition, and a wetting and foam stabilizing composition that forms the paste. This document disclose that the filling and polishing composition comprises greater than about 50% of the tablet and that the carbon dioxide producing composition comprises less than about 25% by weight of the tablet. The tablet is water free to prevent degradation of the stannous fluoride before use. A tablet is chewed to form the paste. The paste is swished around in the mouth and between the teeth to perform a mechanical cleaning action and to bring the stannous fluoride in contact with the tooth surfaces. The tablet then is swallowed. Twice a day use is said to provide an anti-caries and anti-plaque effect greater than that heretofore achieved by any dental hygiene product.

U.S. Pat. No. 8,858,920 discloses an oral care composition that includes xylitol and a water-soluble calcium salt for caries prevention. Methods of treating and preventing dental caries are also disclosed. U.S. Pat. No. 6,207,138 discloses a method and composition for remineralizing teeth wherein the composition contains a mixture of a casein glycomacropeptide and xylitol. U.S. Pat. No. 5,804,165 discloses a non-liquid oral dentifrice composition in the form of powder or tablets that is characterized by an efficacious ratio of carbon dioxide source, xylitol, acid source and silicon dioxide.

U.S. Pat. No. 6,054,119 discloses a dentifrice to protect the teeth, which preparation is anhydrous, with the possible exception of crystal water, and by structure, for example a powder, solid tablet or other anhydrous compositions. The preparation contains a remineralizing component, a pH buffer component, xylitol, and fluoride. Due to the effect of the water contained in the saliva or water added otherwise, the compounds in the preparation react with each other so as to bring about both a remineralization reaction correcting cavity formation in the teeth, and a pH buffering reaction prevention cavity formation in the teeth.

U.S. Patent Application Publication No. 2007/0196477 discloses rapidly disintegrating tablets that include a calcium phosphate material in combination with other common tablet components. Such a calcium phosphate material must exhibit a sufficiently low surface area in order to boost the ability of the table to separate quickly when introduced into a user's mouth cavity. Such a tablet is dimensionally stable prior to use (low friability) and, when immersed in water the tablet disintegrates therein in less than about 60 seconds.

U.S. Pat. No. 6,238,648 discloses oral care compositions, including therapeutic rinses, toothpastes and gels comprising a combination of a non-cariogenic carbohydrate and polyalcohol. This patent further discloses a method for treating or preventing conditions in the mouth that favor formation of tooth caries. U.S. Patent Application Publication No. 2005/0244343 discloses rapidly disintegrating oral care tablets that include a super disintegrant. The tablet comprises a silica; a super disintegrant; and a sugar alcohol. When immersed in water the tablet has a friability of less than about 2% and disintegrates in less than about 60 Seconds.

A rapidly disintegrating tablet also is disclosed in U.S. Patent Application Publication No. 2005/0244492. The tablet comprises: titanium dioxide; a super disintegrant; and a sugar alcohol. When immersed in water the tablet has a friability of less than about 2% and disintegrates in less than about 60 Seconds. U.S. Patent Application Publication No. 2007/0254067 discloses a method of consumer customization of oral care products in which the consumer can select from customization agents to add to a base product.

Single use oral care products that include chewable products are disclosed in U.S. Pat. No. 4,765,984. The single unit dose chewable oral product is stabilized against syneresis and includes an alginate gelling agent, cross-linked with a calcium ion, flavor and a liquid vehicle containing water, humectant and a vegetable oil additive to reduce syneresis. U.S. Pat. No. 4,308,252 discloses a dental prophylaxis tablet containing abrasives and anticaries agents. The tablet is hard enough to withstand normal storage and handling. The tablet also contains dispersing and wetting agents so that it may be readily constituted into a dental prophylaxis paste by the addition of water and may contain sweeteners and flavors. A typical tablet is approximately one gram in weight and has hardness of about 3.5 to 4.0 kilograms (Pfizer tester). A typical tablet can be hydrated in approximately 60 seconds with the addition of water to form a prophylaxis paste. A typical formulation is: feldspar 61%, Cabosil™ 1%, Instant ClearJel™ 5%, StaR 1500™ 25%, sodium saccharin 0.5%, sodium citrate 0.5%, stannous fluoride 5%, Stearowet-C™ 0.5% and flavors 1%.

Multi-part chewing gum tablets containing a variety of ingredients including pharmaceutically active ingredients are disclosed in U.S. Pat. Nos. 8,603,440; 8,623,331; 8,722,022; 8,968,770; and 9,283,191. The disclosures of the all of the documents discussed above, and described below, are incorporated by reference herein in their entireties.

A primary concern for the regular traveler or those working or engaging in sports and away from their residence is the maintenance of regular dental hygiene. This is particularly true for the traveler who may spend many hours without facilities or dental hygiene supplies, such as a toothbrush, dentifrice, mouthwash and dental floss. Most persons note after a few hours, an unpleasant feeling of known bacteria and plaque buildup which is usually accompanied by unpleasant breath, often undetected by the person directly but a condition or risk with which the person is acutely aware. This latter problem has given rise to the increasing popularity of spray type breath deodorizers and "breath mints." The users of such sprays or lozenges fully recognize that the effect is primarily cosmetic or masking and does not attack the real problem of bacteria and plaque removal nor does it provide any cleaning, polishing or improvement in the condition of the surfaces of the teeth, gums, tongue, and surrounding mucosa of the mouth.

There are a number of limitations to good oral hygiene practices for the regular traveler or those working or engaging in sports and away from their residence. One limitation is the unavailability of suitable water and disposal facilities for the actual process associated with the cleaning procedures. Another limitation is the lack of privacy for the procedures of brushing, rinsing, expectoration and cleanup. A third limitation is the lack of reasonable cleanliness. An additional limitation is the lack of convenience of being able to perform the procedures. These principal limitations to good dental hygiene away from home are exemplified by the plight of the business traveler. A 14-hour day of sales calls rarely, if ever, includes a suitable facility with water for brushing, rinsing, expectoration and clean-up. There are few private areas for such procedures. Even if such an area could be found, it is most likely to be in the restroom of a less than frequently cleaned road side filling station, usually inconvenient located, leading to the further frustration of being unable to accomplish any dental hygiene routine or procedure.

There exists a need for a safe, convenient, and effective dental and oral hygiene product that does not suffer from one or more of the limitations discussed above. There also exists a need for such an oral hygiene product that is easy to carry and store for long periods of time, and that is convenient to use even in the presence of others.

BRIEF SUMMARY

Embodiments described herein include an oral hygiene composition that satisfies one or more of these needs. The oral hygiene composition may include natural powders pressed into tablet form that promote the healthy effects of cleaning the teeth, tongue and gums, freshening breath, and removing plaque and buildup, while avoiding risks associated with traditional artificial and/or synthetic ingredients. An additional feature of the embodiments is that the composition avoids the taste of, and does not include sodium bicarbonate as a base. The embodiments provide a xylitol-based pressed tablet to reduce bacteria in the mouth and freshen breath, together with additional ingredients to whiten teeth and protect enamel.

A feature of this disclosure is to provide natural powders pressed into tablet form that provide whitening, freshening and sanitizing similar to that of traditional toothpaste, while avoiding risks associated with artificial and/or synthetic ingredients normally found in toothpaste. The tablets also are more convenient than brushing one's teeth. In accordance with one embodiment, the powder composition includes powdered xylitol and at least one tooth cleaning agent. In another embodiment, the composition further comprises kaolin as an abrasive, which may aid in removing plaque and other buildup from the surface of the teeth, and in another embodiment, the composition may further include fluoride.

Other embodiments including those in which the composition further includes natural flavoring(s), such as peppermint oil or natural whitening ingredients such as activated charcoal or kaolin. In another embodiment, the composition might include aloe vera powder or coconut oil pressed into the tablets for protection of sensitive teeth and gums. Still other embodiments include methods of making the powder composition that includes mixing at least xylitol and a tooth cleaning agent, optionally granulating the xylitol and/or tooth cleaning agent(s), optionally drying the mixture, and pressing the mixture into tablet or capsule form.

Both the foregoing general description and the following detailed description are exemplary and explanatory and are intended to provide further explanation of the embodiments as claimed. Other objects, advantages, and features will be readily apparent to those skilled in the art from the following detailed description of the embodiments.

DETAILED DESCRIPTION

The present disclosure concerns a pressed powder composition, preferably in the form of a tablet or capsule, that can be used for cleaning and brightening the teeth. In one embodiment, the powder composition includes a mixture of natural ingredients with a xylitol base. One of the features of the embodiments is to provide a natural toothpaste alternative, which promotes similar desirable whitening, freshening, sanitizing results of traditional toothpaste, while avoiding risks associated with artificial and/or synthetic ingredients and delivered in a hygienic, convenient and stable way.

Before the compositions, active agents, etc., and methods are described, it is understood that the embodiments are not limited to the particular methodology, protocols, compositions, powders, etc., as these may vary. It also is to be understood that the terminology used herein is for the purpose of describing particular embodiments only, and is not intended to limit the scope of the present embodiments which will be limited only by the appended claims.

Terms and phrases used herein are defined as set forth below unless otherwise specified. Throughout this description, the singular forms "a," "an," and "the" include plural reference unless the context clearly dictates otherwise. Thus, for example, a reference to "a powder" includes a plurality of powders, and a reference to "a natural flavor" is a reference to one or more natural flavors and equivalents thereof known to those skilled in the art, and so forth.

The embodiments described herein preferably provide one or more advantages, in addition to those described previously, selected from: (a) whitening teeth; (b) reducing bacteria in the mouth; (c) including antioxidants; (d) freshening breath; (e) avoiding artificial and/or synthetic ingredients; (f) improving oral health; (g) having a pleasant taste; (h) reducing or eliminating breath odor; (i) neutralizing pH levels in the mouth; (j) neutralizing cariogenic bacterial acids; and removing plaque from the surface of the teeth, bums, tongue and surrounding mucosa in the mouth. These and other advantages of one or more aspects will become apparent from consideration of the ensuing description and accompanying examples. Although the description above contains many specifics, these should not be construed as limiting the scope of the embodiments but as merely providing illustrations of some of several embodiments. Thus the scope of the embodiments should be determined by the claims that are appended and their legal equivalents, rather than by the examples given.

The citation of documents herein does not constitute an admission that those documents are prior art or have any relevance to the patentability of the embodiments disclosed herein. Any discussion of the content of the documents mentioned in the Introduction section is intended merely to provide a general summary of assertions made by the authors of the documents, and does not constitute an admission as to the accuracy of the content of such documents. All documents described in this specification are hereby incorporated by reference in their entirety.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention. As referred to herein, all compositional percentages are by weight of the total composition, unless otherwise specified.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

It is a feature of an embodiment to provide a compressible powder composition that includes powdered xylitol and at least one tooth cleaning agent. In another embodiment, the composition further comprises an abrasive such as kaolin, which may aid in removing plaque and other buildup from the surface of the teeth, and in another embodiment, the composition may further include fluoride. It also is a feature of the embodiments to provide the powder composition in the form of a compressed tablet or capsule. In addition, it is a feature of an embodiment to provide a method of making a compressed tablet or capsule that includes powdered xylitol and at least a tooth cleaning agent.

Xylitol is a non-cariogenic carbohydrate and has a variety of uses including, but not limited to, a non-cariogenic sweetener, a humectant, and an anti-caries agent. While not intending to be bound by any particular theory, xylitol appears to cause a disturbance in the metabolism of fermentable carbohydrates by *S. mutans* and thereby decreases plaque formation and reduces plaque adhesion to the pellicle. Also, upon metabolizing xylitol, the toxic metabolite xylitol-5-phosphate forms within the *S. mutans* cells which may interfere with glycolysis energy production and may also involve an energy-consuming futile cycle. The energy consuming cycle kills the *S. mutans* which results in reduced caries. Any xylitol may be used in accordance with the embodiments, including xylitol readily available for sale on consumer web sites (e.g., Amazon, etc.), or commercial grade, directly compressible xylitol (DC xylitol) can be used. Xylitol may be present in the powder at about 10% to about 40% by weight, or from about 15% to about 30% by weight, or from about 20% to about 25% by weight, based on the total weight of the composition.

The compositions also may contain additional anti-caries agents, and taste-masking agents such as erythritol. Erythritol can be about 60% as sweet as sucrose at practical use levels and is sweeter than mannitol and sorbitol, which are only 50% as sweet as sucrose under similar conditions. It has an advantage over propylene glycol and glycerol in having a clean and pleasant taste and it is very soluble in water (a saturated solution contains about 38% w/w). Unlike other polyols, erythritol is not significantly metabolized after oral ingestion in humans, and so is of unique interest as a non-nutritive sweetening agent. Commercially available erythritol is prepared as a white crystalline product by treating an aqueous alkali carbonate solution of 2-buten-1,4-diol with chlorine and saponifying the resulting chlorohydrin. The natural product can be produced on a commercial scale by propagating specially selected yeast strains in appropriate aqueous nutrient media. Any erythritol may be used in accordance with the embodiments, including erythritol readily available for sale on consumer web sites (e.g., Amazon, etc.), or commercial grade, directly compressible erythritol (DC erythritol) can be used. Erythritol may be present in the powder at about 10% to about 40% by weight, or from about 15% to about 30% by weight, or from about 20% to about 25% by weight, based on the total weight of the composition.

The oral hygiene compositions described herein contain at least one tooth cleaning agent, and more preferably contain more than one tooth cleaning agent. Tooth cleaning agents include those commonly known in the art that are effective in cleaning teeth, such as abrasives, polishing agents, whitening agents, anti-bacterial agents, anti-fungal agents, anti-caries agents, etching agents, forming agents, surfactants, flavoring agents, coloring agents, and the like. The oral hygiene compositions also may contain additional components that are typically used in oral hygiene compositions and products.

An abrasive often provides a cleaning action for oral care products including the removal of plaque, food debris, and the like. The abrasive should not damage the enamel of teeth, and it should have compatibility with other components of the composition. Suitable abrasives for use in the embodiments can be selected from materials that do not cause excessive erosion of tooth dentin leading to tooth sensitivity such as calcium phosphate materials, including calcium pyrophosphate, tribasic calcium phosphate, dibasic calcium phosphate dihydrate and anhydride, and calcium carbonate, as well as silica and aluminum hydroxide. In addition to those materials, natural fibrous materials such as cellulose and derivatives thereof, and natural materials such as shell powders of eggs and shellfish may also be used as the abrasive.

The calcium phosphate material preferably is a calcined calcium phosphate material. Suitable pre-calcined calcium phosphates include dicalcium phosphate, also known as dibasic calcium phosphate, both anhydrous (DCP) and dihydrate (DCPD) forms; tricalcium phosphate (TCP), also known as tribasic calcium phosphate; calcium pyrophosphate; calcium polyphosphate and the like, and combinations of more than one calcium phosphate. Two potentially preferred calcium phosphates are calcined (defined herein as heating for up to 2 hours at 900° C.) EMCOMPRESS™ dicalcium phosphate dehydrate which has a surface area of about 4 $m^2/g$, and calcined TRI-CAFOS® P tricalcium phosphate which has a surface area of about 6 $m^2/g$. In one embodiment, the composition includes the calcium component, preferably dicalcium phosphate, in an amount of from about 10% to about 40% by weight, or from about 15% to about 30% by weight, or from about 20% to about 25% by weight, based on the total weight of the composition.

The composition may further comprise a fluoride-providing agent or a fluoride-ion source that can be used as anti-caries agents. The fluoride-providing agents typically should be sufficiently water soluble to release an anti-caries amount of fluoride ions in water or the saliva. Suitable fluoride-providing agents are organic or inorganic. Inorganic fluoride ion-providing agents include metal, alkali metal, alkaline earth metal and ammonium salts of fluoride, such as for example potassium fluoride, sodium fluoride, ammonium bifluoride, calcium fluoride, a copper fluoride such as cuprous fluoride, barium fluoride, sodium fluorosilicate, ammonium fluorosilicate, sodium fluorozirconate, sodium monofluorophosphate, aluminum mono- and di-fluorophosphate, fluorinated sodium calcium pyrophosphate, stannous fluoride, lithium fluoride, cesium fluoride, aluminum fluoride, cupric fluoride, indium fluoride, stannous fluorozirconate, ferric fluoride, nickel fluoride, palladium fluoride, silver fluoride, zirconium fluoride, and mixtures thereof. Preferred inorganic fluoride ion-providing agents are sodium monofluorophosphate and sodium fluoride.

Organic fluoride ion-providing agents include hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolamineoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, δ8-9 octadecenylbenzyldimethylammonium fluoride, dioctyldiethylammonium fluoride, cyclohexylcetyldimethylammonium fluoride, furfuryllauryidimethylammonium fluoride, phenoxyethylcetyldimethylammonium fluoride, N:N'-tetramethyl-N:N'-dilaurylethylenediammonium difluoride, N-cetylpyridinium fluoride, N:N-dilauryl-morpholinium fluoride, N-myristyl-N-ethylmorpholinium fluoride, N-(octylaminocarbonylethyl)-N-benzyldimethylammonium fluoride, N—(B-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-cicosyldimethylammonium fluoride, olaflur (N'-octadecyltrimethylendiamine-N,N,N'-tris(2-ethanol)-dihydrofluoride), betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, and mixtures thereof.

The fluoride-providing agent, if present, may be present in an amount sufficient to release between about 200 ppm to 3000 ppm fluoride ion, preferably from about 800 to about 1500 ppm fluoride ion. The fluoride-providing agent may be present in the composition from about 0.001% to about 3% by weight.

The powder compositions also may include a forming agent and/or a surfactant to not only clean teeth, but also to assist in the formation of bubbles. Generally, the forming agent may include an anionic surfactant, a cationic surfactant, a non-ionic surfactant, an amphoteric surfactant, or a zwitterionic surfactant. The forming agent may be a single material or a combination of two or more materials. Suitable forming agents include, for example, a safe and effective amount of sodium lauryl sulfate, sodium coconut monoglyceride sulfonate, sarcosinate, e.g. sodium lauroyl sarcosinate, taurate, sodium lauryl sulfoacetate, sodium lauroyl isethionate, sodium laureth carboxylate and sodium dodecyl benzene sulfonate. In addition, cocamidopropyl betaine, Poloxamer, sorbitan monooleate, PEG-40 sorbitan isostearate or a mixture thereof may also be used as the surfactant.

It is preferred that the powder composition not contain sodium lauryl sulfate, although if used, the amount of sodium lauryl sulfate should be less than 5% by weight, or less than about 4%, or less than about 2%, or less than about 1% by weight. It is advantageous instead to use sarcosinate or sodium lauryl sulfoacetate. In one embodiment, the composition includes the forming agent, preferably sodium lauryl sulfoacetate, in an amount of from about 5% to about 30% by weight, or from about 10% to about 20% by weight, or from about 13% to about 16% by weight, based on the total weight of the composition.

In addition to the calcium phosphate material, the powder compositions may contain other calcium-containing compounds, including natural calcium-containing compounds that can be used as an abrasive. An embodiment therefor includes a powder composition that includes kaolin, or calcined kaolin, or purified calcined kaolin, such as the kaolin described in, for example, U.S. Pat. No. 4,122,163, the disclosure of which is incorporated by reference herein in its entirety. In one embodiment, the composition includes the natural calcium-containing compound, preferably kaolin, in an amount of from about 1% to about 30% by weight, or from about 5% to about 20% by weight, or from about 8% to about 12% by weight, based on the total weight of the composition.

The powder compositions also may contain additional abrasive ingredients such as sodium bicarbonate or stabilized sodium percarbonate. The sodium bicarbonate ingredient of the embodiments functions as a soft abrasive, and additionally it imparts a clean and fresh feel in the oral cavity when a toothpaste formulation is utilized. The sodium bicarbonate preferably has an average particle size between about 5-200 microns. Because of the bitter taste of sodium bicarbonate, if it is used in the powder compositions, it is used in amounts less than 20%, or less than about 10%, or less than about 5% by weight, based on the total weight of the composition. In some embodiments, sodium bicarbonate is used in amounts within the range of from about 0.1% to about 10% by weight, or from about 1% to about 5% by weight, or from about 2% to about 4% by weight, based on the total weight of the composition.

The powder compositions of the embodiments also may contain flavorants, colorants, dyes, natural preservatives, and the like. In an embodiment, the contain flavorants, colorants, dyes, etc., may be selected from natural materials, and preferably are extracts of plant materials. Suitable ingredients may contain, for example, a natural mint flavoring product obtained from a plant of the Menthe genus and the Lamiaceae family, or an artificial counterpart of the natural product. L-Menthol has a unique refreshing taste, a minty odor and a pronounced cooling effect on the skin and mucosa. L-Menthol is the main constituent of the peppermint oils from *Mentha arvensis* (content: 70 to 80%) and *Mentha piperita* (content: 50 to 60%). L-Menthol can be obtained from the crude peppermint oil by crystallisation. In some embodiments, the powder composition contains menthe in the form of menthol crystals in an amount of from about 0.01% to about 5% by weight, or from about 0.1% to about 3% by weight, or from about 1% to about 3% by weight, based on the total weight of the composition.

Suitable natural preservatives may include, for example, any ingredient such as a solid, liquid, vapor, extract, compound, derivative, bioactive component(s), etc. from any part of; a seed, root, rhizome, leaf, bark, plant, fruit and/or vegetable consisting of at least one of the following: Agave (Genes *Agave*), Algae (*Spirulina*), Allium Family (Onions, Garlic, Chives, Leeks, Shallots and Scallions), Amla (*Phyllanthus emblica*), Apple (*Malus domestica*), Apricot (*Prunus armeniaca*), Araca-Boi (*Eugenia stipitata*), Aronia (*Aronia melanocarpa*), Artichokes (*Cynara cardunculus*), Arugula (*Eruca sativa*), Ashwagandha (*Withania somnifera*), Avocado (*Persea gratissima*), Banana (*Musa* spp.), Barley Grass (*Hordeum vulgare*), Bell Peppers (*Capsicum frutescens*), Beet (*Beta vulgaris*), Bergamot (*Citrus bergamia*), Bilberry (*Vaccinium myrtillus*), Bitter Yam (*Dioscorea bulbifera*), Blackberry (*Rubus villosus*), Black Johannisberry (Genes *ribes*), Boysenberry (*Rubus ursinus×idaeus*), Broccoli (*Brassica oleracea italica*), Broccoli Rabe (*Brassica rapa*), Brussels Sprouts (*Brassica oleracea* var. *gemminfera*), Cabbage (*Brassica oleracea* var. *capitata*), Cauliflower (*Brassica oleracea* var. *botrytis*), Caja (*Spondias dulcis*), Camu-Camu (*Myrciaria dubia*), Cantaloupe (*Cucumis melo*), Carrot (*Daucos carota*), Cashew (*Anacardium occidentale*), Celery (*Apium graveolens*), Chamomile (*Matricaria recutita* and *Chamaemelum nobile*), Cherry (*Prunus cerasu*), Chili (*Rosa roxburghii*), Chinese Goldthread (*Coptis chinensis* franchinflorescence), Choriyanam (*Tragia involucrate*), Cocoa (*Theobroma cacao*), Coconut Milk (*Cocus nucifera*), Coconut Water, Coffee (*Coffea arabica*), Coffeeberry, Cranberry (*Vaccinium macrocarpon*), Crenshaw (*Cucumis melo*), Cucumber (*Cucumis sativa*), Cupuacu (*Theobroma grandiflorum*), Dates (*Phoenix dactylifera*), Dragon Fruit (*Hylocereus undatus*), Elderberry (*Sambucus nigra*), Fig (*Ficus glomerata*), Gac (*Momordica cochinchinensis*), Ginger (*Zingiber officinalis*), Ginseng (*Panax ginseng*), Golden Root (*Rhodiola rosea*), Graviola (*Annona muricata*), Grapefruit (*Citrus paradisi*), Greenbean (*Phaseolus vulgaris*), Guarana (*Paullinia cupana*), Guava (*Psidium guajava*), Guavasteen (*Feijoa sellowiana*), Honeydew (*Cucumis melo*), Indian Kudzu (*Pueraria tuberosa*), Jiaogulan (*Gynostemma pentaphyllum*), Juniper (*Juniperus communis*), Kale (*Brassica oleracea*), Kiwi (*Actinidia chinensis*), Lemon (*Citrus limonum*), Licorice (*Glycyrrhiza glabra*), Lingonberry (*Vaccinium vitis-idaea*), Loganberry (*Rubus loganobaccus*), Lulo (*Solanum quitoense*), Maitake Mushroom (*Grifola frondosa*), Mango (*Mangifera indica*), Maralu (*Rhaponticum carthamoides*), Marking Nut Tree (*Salacia reticulata*), Miracleberry (*Synsepalum dulcificum*), Mulberry (*Morus alba, Morus rubra, Morus nigra*), Mulberry (*Morus alba, Morus rubra, Morus nigra*) With 1-deoxynojirimycin (DNJ), Muskmelon (*Cucumis melo*), Nashi (*Pyrus pyrifolia*), Nectarine (*Prunus persica*), Neem (*Azadirachta indica*), Noni (*Morinda citrifolia*), Olive (*Elaeagnus angustifolia*), Orange (*Citrus aurantium*), Papaya (*Carica papaya*), Parsley (*Petroselinum crispum*), Passion Flower (*Passiflora incarnate*), Passion Fruit (*Passiflora edulis*), Peach (*Prunus persica*), Pear (*Pyrus communis*), Pepper (*Piper nigrum*), Persimmon (*Diospyros virginia*), Pineapple (*Ananas comosus*), Pinyin (*Schisandra chinensis*), Plum (*Prunus umbellate*), Prune (*Prunus domestica*), Pumpkin (*Cucurbita pepo*), Quebracho (*Aspidosperma quebracho-blanco* & *Schinopsis lorenzii*), (Quince (*Cydonia oblonga*), Raisins (*Vitis vinifera*), Raspberry (*Rubus idaeus*), Red Wine, Rhubarb (*Rheum rhabarbarum*), Spinach (*Spinacia oleracea.*), Sprout (*Brassica oleracea gemmifera*), Soy (*Glycine max*), Star Fruit (*Averrhoa carambola*), Strawberry (*Fragaria virginiana*), Sun Flower (*Helianthus annuus*), Sweet Potato (*Ipomoea batatas*), Swiss Chard (*Beta vulgaris*), Tangerine (*Citrus reticulate*), Tarragon (*Artemisia dracunculus*), Tomato (*Solanum lycopercicum*), Turnips (*Brassica rapa*), Velvet Bean (*Mucuna pruriens*), Watermelon (*Citrullus vulgaris*), Watercress (*Nasturtium officinale*), Winter Cherry (*Withania somnifera*), Yohimbe (*Pausinystalia johimbe*), Yumberry (*Myrica rubra*) and Yuzu (*Citrus ichangensis×C. reticulata*).

Particularly preferred natural ingredients include *Mentha piperita* (peppermint oil), *Citrus sinensis* (sweet orange oil), and combinations thereof. When used in the powder compositions, the natural preservatives and flavorants can be used in relatively minor amounts ranging from about 0.0001% to about 0.1%, or any value therebetween.

The powder compositions may be formulated into a tablet by mixing at least xylitol and a tooth cleaning agent, optionally granulating the xylitol and/or tooth cleaning agent(s), optionally drying the mixture, and pressing the mixture into tablet or capsule form. The tablet may be prepared by mixing powdered materials and compacting the mixed powder in a press to form a tablet. Alternatively, the tablet may be prepared by mixing a combination of powder materials and liquid or gel materials, granulating the mixture or spray drying the liquid onto the powder material. Other methods of mixing the components of the powder composition also may be used, as will be appreciated by those skilled in the art. For example, granulators, blenders, fluid bed granulators, mixing devices for liquids and powders, grinders, and the like can be used.

The components should be sufficiently ground to an appropriate mesh size to be suitable for tableting. The components may have an average particle size within the range of from about 1 to about 1,000 µm, or from about 100 to about 800 µm, or from about 150 to about 600 µM. The various components may have the same, similar, or different particle sizes and particle size distribution. Those skilled in the art will be capable of determining the appropriate mesh size of the various components, as well as the ultimate blend, to achieve the appropriate strength in the tablet. See, e.g., Sun, et al., "Particle Size Specifications for Solid Oral Dosage Forms: A Regulatory Perspective," *Am. Pharm. Rev.*, Vol. 13(4) (2010).

Typically, the compositions described herein can be mixed in dry form to form a uniformly dispersed powdered mixture and then tableted on a tableting machine, of a type known in the art, to a suitable hardness. The tablets may be of any convenient type, size, shape, or the like. Tablets of ½-2 grams each usually are sufficient, and one or more tablets may be consumed at a time, as required. Hardnesses in the range of about 3 to 8 kilograms crushing strength are satisfactory. It will be appreciated that the hardness (strength) of the tablets should be effective to maintain the structural integrity of the tablets throughout production, packaging, handling, transportation, storage and use to maintain a consistent dosage and tablet size. In addition, the tablet should be hydratable and must retain the ability to hydrate throughout the above conditions.

The tablet may optionally be coated with a coating material such as waxes, shellac, carboxymethyl cellulose, polyethylene/maleic anhydride copolymer or kappa carrageenan to further increase the time it takes the tablet to dissolve in the mouth. An uncoated tablet is slow-dissolving, providing a sustained release rate of active ingredients of about 3 to 5 minutes, depending upon the size of the tablet.

Illustrative embodiments of the invention are described below. The showings are for purposes of illustrating preferred embodiments and not for purposes of limiting the same. The following explanation provides specific details for a thorough understanding of an enabling description for these embodiments. One skilled in the art will understand that the invention may be practiced without such details. In other instances, well-known structures and functions have not been shown or described in detail to avoid unnecessarily obscuring the description of the embodiments.

EXAMPLES

In order to more adequately describe what the inventor regards as her invention, the following example is provided. It should be understood that the formulations set forth in the Example are not to be construed as limiting of the scope of the invention, except so far as they yield natural tooth powders having desired properties and characteristics to not only clean teeth but have the ability to be pressed into tablets.

The following table provides an exemplary tablet formulation of the same with the percentages given by weight of the toothpaste.

TABLE 1

| Ingredient | Weight percent |
| --- | --- |
| Dicalcium phosphate | 23.45 |
| Xylitol | 23.45 |
| Erythritol | 23.45 |
| Sodium Lauryl Sulfoacetate | 15.64 |
| Kaolin | 9.12 |
| Sodium bicarbonate | 3.26 |
| Menthe (menthol crystals) | 1.63 |
| *Mentha piperita* (Peppermint Oil) | q.s. |
| *Citrus sinensis* (Sweet Orange Oil) | q.s. |

The materials were processed and tableted using bench-scale devices. Those skilled in the art will appreciate that industrial scale equipment could be used, as well as commercial grade readily compressible ingredients. The xylitol and erythritol were ground in a hand held salt grind attached to a hand drill. The particle size of the xylitol, erythritol, and menthol were about 600 μm, or at or about 30 Mesh. Commercially available xylitol and erythritol were used.

Commercially available Menthe (menthol crystals—1R, 2S,5R-2-isopropyl-5-methylcyclohexanol) then was ground using a mortar and pestle, and sifted through an approximately 30 Mesh sieve to provide menthe granules having a particle size of about 600 μm. The menthe, xylitol, and erythritol then were combined with the remaining dry ingredients, dicalcium phosphate, kaolin, sodium lauryl sulfoacetate, and sodium bicarbonate in a plastic container, the container was enclosed with a lid and then shook by hand for about 3 minutes until properly mixed. The essential oils (peppermint and sweet orange) then were added to the dry mixture in the plastic container, and the material was mixed by hand to crumble the materials together, and then shaken for about 2 minutes until fully blended.

The mixed components then were tableted using a tabletop tablet press, TDP 5 Desktop Tablet Press from LFA Machines Oxford Ltd. The tooth powder tablets then were made using a 0.4 gram, 20 mm diameter size tablet setting, with a circular, beveled edge die. The components were subjected to a maximum pressing pressure of about 50 Kn.

Particularly preferred embodiments have been described herein. Those skilled in the art will appreciate that various modifications may be made to the formulation, as well as its method of manufacture, without departing from the spirit and scope of the embodiments.

What is claimed is:

1. A powder composition consisting essentially of:
    (a) from about 20% to about 25% by weight powdered xylitol;
    (b) from about 15% to about 30% by weight erythritol;
    (c) from about 10% to about 40% by weight of at least one abrasive tooth cleaning agent comprising a combination of from about 20% to about 25% of dicalcium phosphate, and from about 2% to about 4% by weight of sodium bicarbonate, wherein the amounts are by weight of the composition;
    (d) at least one additive selected from the group consisting of a flavorant, a colorant, a dye, a natural preservative, and mixtures thereof, and
    (e) from about 5% to about 30% by weight sodium lauryl sulfoacetate
    wherein the composition does not contain sodium lauryl sulfate.

2. The powder composition according to claim 1, wherein the composition is in the form of a compressed tablet.

3. The powder composition according to claim 1, further comprising an additional tooth cleaning agent selected from the group consisting of polishing agents, whitening agents, anti-bacterial agents, anti-fungal agents, anti-caries agents, etching agents, forming agents, surfactants, and mixtures thereof.

4. The powder composition according to claim 1, further comprising a second abrasive tooth cleaning agent selected from natural calcium-containing compounds and sodium bicarbonate.

5. The powder composition according to claim 4, wherein the natural calcium-containing compound is kaolin and is present in an amount of from about 1% to about 30% by weight, based on the total weight of the composition.

6. A powder composition consisting essentially of:

| Ingredient | Weight percent |
| --- | --- |
| Dicalcium phosphate | 23.45 |
| Xylitol | 23.45 |
| Erythritol | 23.45 |

-continued

| Ingredient | Weight percent |
|---|---|
| Sodium Lauryl Sulfoacetate | 15.64 |
| Kaolin | 9.12 |
| Sodium bicarbonate | 3.26 |
| Menthe (menthol crystals) | 1.63 |
| *Mentha piperita* (Peppermint Oil) | q.s. |
| *Citrus sinensis* (Sweet Orange Oil) | q.s. | wherein the weight percentages are based on the total weight of the powder composition.

7. The powder composition according to claim 6, wherein the composition is a compressed tablet.

\* \* \* \* \*